US008675885B2

(12) United States Patent
Sapiejewski

(10) Patent No.: US 8,675,885 B2
(45) Date of Patent: Mar. 18, 2014

(54) ADJUSTING NOISE REDUCTION IN HEADPHONES

(71) Applicant: Bose Corporation, Framingham, MA (US)

(72) Inventor: Roman Sapiejewski, Boston, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 13/661,521

(22) Filed: Oct. 26, 2012

(65) Prior Publication Data

US 2013/0129106 A1 May 23, 2013

Related U.S. Application Data

(60) Provisional application No. 61/562,524, filed on Nov. 22, 2011.

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 29/00*** | (2006.01) |
| ***H04R 1/10*** | (2006.01) |

(52) U.S. Cl.
USPC ........... 381/71.6; 381/58; 381/74; 381/71.12; 381/71.1

(58) Field of Classification Search
USPC ................. 381/71.6, 58, 123, 71.1, 71.12, 74
See application file for complete search history.

(56) References Cited

U.S. PATENT DOCUMENTS

| | | | | |
|---|---|---|---|---|
| 5,185,807 | A * | 2/1993 | Bergin et al. | 381/378 |
| 6,118,878 | A * | 9/2000 | Jones | 381/72 |
| 6,704,428 | B1 | 3/2004 | Wurtz | |
| 2008/0175406 | A1 | 7/2008 | Smith | |
| 2009/0323978 | A1 | 12/2009 | Leske et al. | |
| 2010/0189303 | A1 | 7/2010 | Danielson et al. | |
| 2011/0044463 | A1 | 2/2011 | DiRusso | |

FOREIGN PATENT DOCUMENTS

| | | | |
|---|---|---|---|
| JP | 08079874 | A | 3/1996 |
| WO | 0035243 | A2 | 6/2000 |

OTHER PUBLICATIONS

Sennheiser S1 Digital Aviation Headset, retrived from http://www.sennheiser-aviation.com/aviation-headsets-pilot-flight_active-noise-reduction_504212?print on Jan. 22, 2013.

International Search Report and the Written Opinion of the International Searching Authority dated Feb. 13, 2013 for PCT/US2012/064759.

* cited by examiner

*Primary Examiner* — Xu Mei
*Assistant Examiner* — Douglas Suthers

(57) ABSTRACT

A headset includes first and second earcups each having a front opening adapted to be adjacent to a respective ear of a user and including an electroacoustic transducer, a headband coupled to each of the earcups, and an active noise reduction circuit coupled to the electroacoustic transducers. The headband is configurable between at least two configurations that each press the earcups against the head of the user with different amounts of force. The active noise reduction circuit is configured to determine which of the at least two configurations the headband may be configured in, to provide a different amount of noise reduction when the headband may be configured in each of the different amounts of force, and to automatically transition between the different amounts of noise reduction in response to a change in the configuration of the headband between the at least two configurations.

62 Claims, 3 Drawing Sheets

ADJUSTING NOISE REDUCTION IN HEADPHONES

PRIORITY CLAIM

This application is a continuation of and claims priority to U.S. Provisional Patent Application 61/562,524, the entire contents of which are incorporated by reference.

BACKGROUND

This disclosure relates to adjusting noise reduction in headsets or headphones.

Active noise reduction (ANR) headphones, such as those described in U.S. Pat. No. 7,412,070, use electronics to create anti-noise signals that cancel the ambient noise as it reaches the wearer's ear. Headphones that contact the head around the ear are referred to as circum-aural, while those that rest directly on the external ear, also known as the pinna of the ear, are referred to as supra-aural. ANR headphones may be circum-aural, supra-aural, or in-the-ear, and typically employ some passive noise reduction measures to provide noise reduction beyond the bandwidth and energy level provided by the active electronics. A set of circum-aural headphones 10 is shown in FIG. 1A for reference. Such headphones have two earcups 12 and 14, each with a cushion 16, 18 that contacts the wearer's head. In supra-aural headphones, the cushions would contact the wearer's external ear. The earcups 12 and 14 are connected to each other by a headband 20 via yokes 22 and 24. Other configurations are also used, such as a direct connection between the end of the headband and the earcups, without a yoke, or a band referred to as a "nape band" that goes behind the wearer's neck rather than over the head.

ANR headphones may use feedback, feedforward, or some combination of the two to generate the anti-noise signals, as shown, for example, in FIG. 1B. In the example of FIG. 1B, an ANR circuit 100 receives input from a feed-forward microphone 102, a feedback microphone 104, and an audio input 106. Implementations may include any or all of these or additional inputs. The signals from the feedforward and feedback microphones are passed through filters 108 and 110 which produce anti-noise signals. The anti-noise signals are combined with any audio input signals, as indicated by summing node 112, amplified by an amplifier 114, and provided as output signals 116 to an electroacoustical transducer 118, also known as a driver or speaker. In some examples, more than one output transducer is used. ANR headphones may also provide audio for entertainment and communication, and may use the same or additional speakers as are used for generating the anti-noise signal to do so. ANR headphones may also reproduce sounds detected by microphones on the exterior of the earcup to allow the user to hear sounds in the environment when desired. This feature is sometimes called talk-through. Feedforward ANR headphones that provide talk-through features may use the same microphones for both feedforward noise cancellation and talk-through, or may have separate microphones for each feature. The signal paths and relative locations and numbers of components in FIG. 1B are merely one example. The various signal paths, such as feedforward and feedback, may each have dedicated amplifier stages applying different gains. ANR circuit 100 may be implemented in analog or digital electronics, or some combination of both.

Passive noise reduction headsets use mechanical measures to reduce the amount of ambient noise reaching the ear of the wearer. These mechanical measures generally consist of acoustic insulation that is placed in the earcups or that is placed in the ear to block the ear canal. For supra-aural and circum-aural headsets, a major factor affecting the amount of noise reduction, beyond the properties of the insulating material itself, are how well the earcups seal to the ears or head of the wearer. The force applied to press the earcups against the wearer's head, referred to as clamping force, is one of several factors that affects the quality of the seal. Other factors are the compliance of the cushion between the earcup and the ear or head, and whether any leaks exist, either between the cushion and the wearer or through parts of the earcup. In some examples, leaks are intentionally provided in order to control the acoustic properties of the headset. Passive noise reduction headsets may include electronic components for reproducing audio, for any or all of entertainment audio, electronic communications, or to provide talk-through using external microphones.

SUMMARY

In general, in one aspect, a headset includes first and second earcups each having a front opening adapted to be adjacent to a respective ear of a user and including an electroacoustic transducer, a headband coupled to each of the earcups, and an active noise reduction circuit coupled to the electroacoustic transducers. The headband is configurable between at least two configurations that each press the earcups against the head of the user with different amounts of force. The active noise reduction circuit is configured to determine which of the at least two configurations the headband may be configured in, to provide a different amount of noise reduction when the headband may be configured in each of the different amounts of force, and to automatically transition between the different amounts of noise reduction in response to a change in the configuration of the headband between the at least two configurations.

Implementations may include one or more of the following features. The headset may include a sensor disposed on the headband to detect the headband configuration. The headset may include a sensor disposed inside the first earcup to detect the amount of force with which the earcup may be pressed against the head of the user. The active noise reduction circuit may be configured to determine the headband configuration based on signals received from a microphone. The headband may also include a user-actuated adjustment control to select between the different amounts of force. The amount of force applied by the headband may be controlled electronically. For a first amount of force applied by the headband, the active noise reduction circuit may provide no noise reduction. The headset may also include a power supply and control electronics, the control electronics configured to decouple the power supply from the active noise reduction circuit when the headband may be applying the first amount of force, and to couple the power supply to the active noise reduction circuitry when the headband may be applying a second amount of force. The second amount of force may be less than the first amount of force. The control electronics may include a switch activated by adjustment of the amount of force applied by the headband. The active noise reduction circuit may also be configured to apply noise reduction having a different frequency response when the headband is configured in each of the different amounts of force.

The active noise reduction circuit may have at least two modes, the first mode providing a first amount of noise reduction when the headband is configured to provide a first amount of force, and the second mode providing a second amount of noise reduction when the headband is configured to provide a second amount of force, the second amount of noise reduction reducing more total noise than the first amount of noise reduction, and the second mode reducing low-frequency noise to a greater extent than the first mode, and reducing high-frequency noise to the same extent as the first mode. The active noise reduction circuit may also be configured to control the frequency response of the overall noise reduction of the headset such that the overall frequency response is generally independent of the amount of force applied by the headband. The active noise reduction circuit may also be configured to control the frequency response of the overall noise reduction of the headset such that the dynamic range of the overall noise reduction of the headset is generally independent of the amount of force applied by the headband. The first and second earcups may each be coupled to a respective first and second cushion sized such that the cushions couple the earcups to the head of the user around the user's ears. The first and second earcups may each be coupled to a respective first and second cushion such that the cushions couple the earcups to the pinnas of a user's ears.

Advantages include providing noise reduction that is appropriate for a given environment, balancing comfort and situational awareness against the need for noise protection.

Other features and advantages will be apparent from the description and the claims.

DESCRIPTION

Figure 1A:
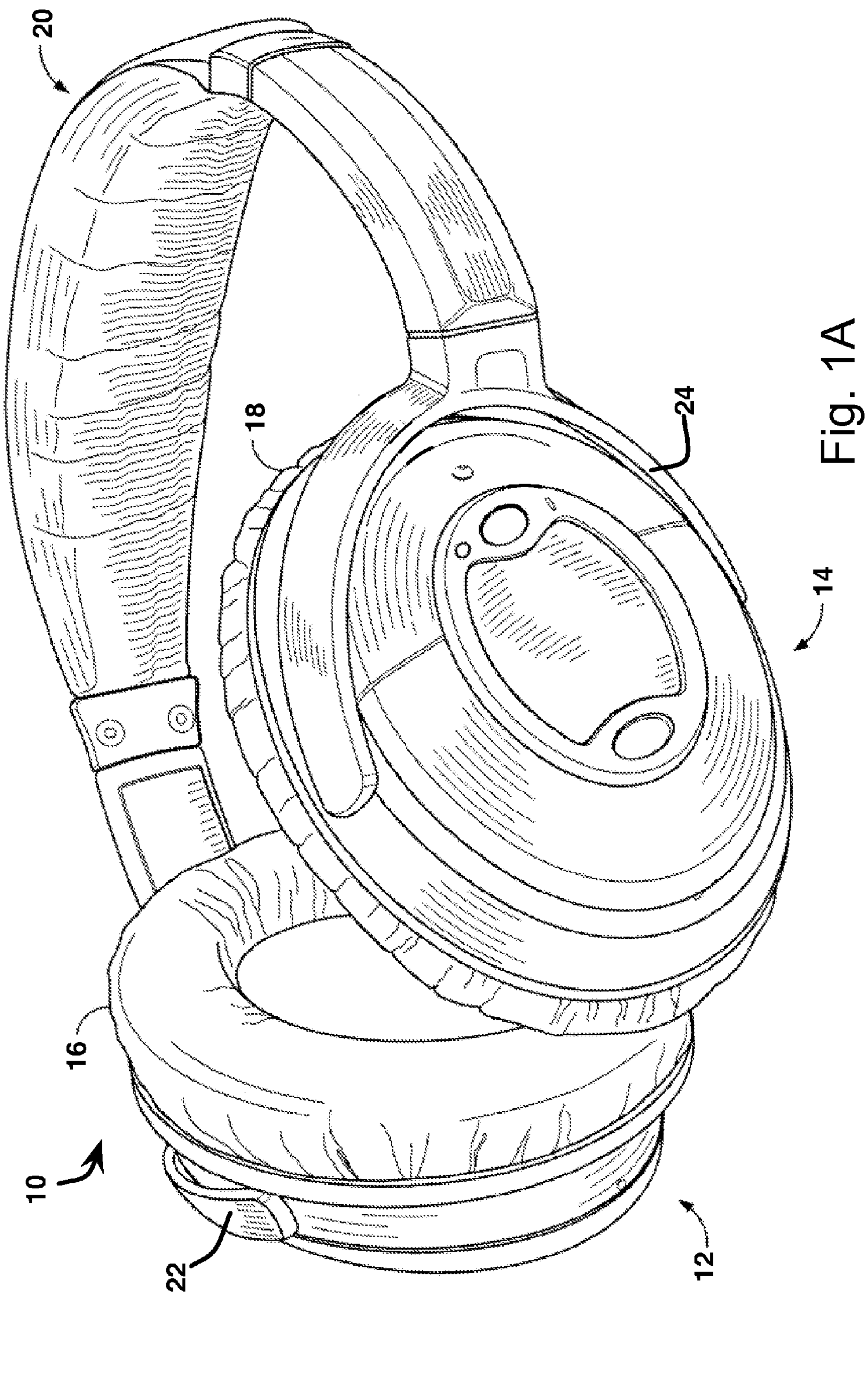
FIG. 1A shows a set of headphones.

Providing high levels of passive noise reduction often leads to headsets and headphones that are uncomfortable to wear for extended periods. This is especially problematic for users in roles where headsets need to be worn for extended periods, such as soldiers, factory workers, and pilots. This comfort can be improved by compromising noise reduction when it isn't needed, such as by loosening the fit of the headset when the ambient noise is reduced. This may be done, for example, during a break on the factory floor or after takeoff in an aircraft. For active noise reduction (ANR) headsets, however, loosening the headset may increase the compliance of the air within the earcup, requiring more power for the ANR circuit to provide the same level of active noise reduction. It can also lead to over-driving of the transducer of the feedback loop, causing or other audible problems.

The amount of passive attenuation provided by a headset is affected by the clamping force because the clamping force controls the quality of the seal between the cushion and the wearer's head. The quality of the seal relates to the amount of air leaking between the cushion and the head. For a typical, compliant cushion, increasing the clamping force produces a corresponding decrease in leakage. That is, doubling the clamping force cuts the amount of leak about in half. Cutting the amount of leak in half may increase passive attenuation by up to 6 dB. In an otherwise ideal system, increasing the clamping force by a factor of 10 would decrease the leak by 90%, and increase passive attenuation by 20 dB. Of course, increasing the clamping force by a factor of 10 would generally be very uncomfortable. For a typical headset, however, cutting the clamping force in half may provide a significant increase in comfort, and only costs 6 dB of passive attenuation. In some examples, that 6 dB may be recovered through adjustment of active noise reduction circuits, though there are trade-offs, as discussed below.

If an active noise reducing (ANR) headset is to be loosened, there are several competing concerns for adjustment of the ANR circuit. As noted above, the increased compliance of the front cavity, due to the increased leakage between the cushion and head, allows over-driving of the output transducer while at the same time requiring increased pressures from that driver to cancel sound. The over-driving problem can be addressed by decreasing the gain of the ANR circuit, but this decreases the output level of the system, making it less-able to cancel the ambient noise at the same time that the passive attenuation has also been reduced. Providing the same level of noise reduction that was achieved with a tight fit would require increasing the gain of the ANR circuit, which can lead to overdriving or clipping (preventing overdriving by cutting power before it happens). These two alternatives may be balanced against another factor, the dynamic range of the ANR circuit.

The dynamic range of an ANR system describes the range of sounds it can cancel. Increasing the gain of the ANR system, while keeping it stable, may provide enough increased cancellation to compensate for the loose fit, but it will decrease the dynamic range of the system. In particular, it will lose the ability to cancel loud, low-frequency noise. If dynamic range is to be preserved, the gain of the ANR system may be decreased. This will provide less overall attenuation, but it will keep its tonal balance and avoid over-driving. Given these tradeoffs, an adjustable headset may then be designed that provides two modes—a first mode offering good dynamic range and good attenuation, but higher clamping force resulting in a less-comfortable fit, and a second mode that compromises dynamic range and attenuation to improve comfort by decreasing the clamping force.

Figure 2:
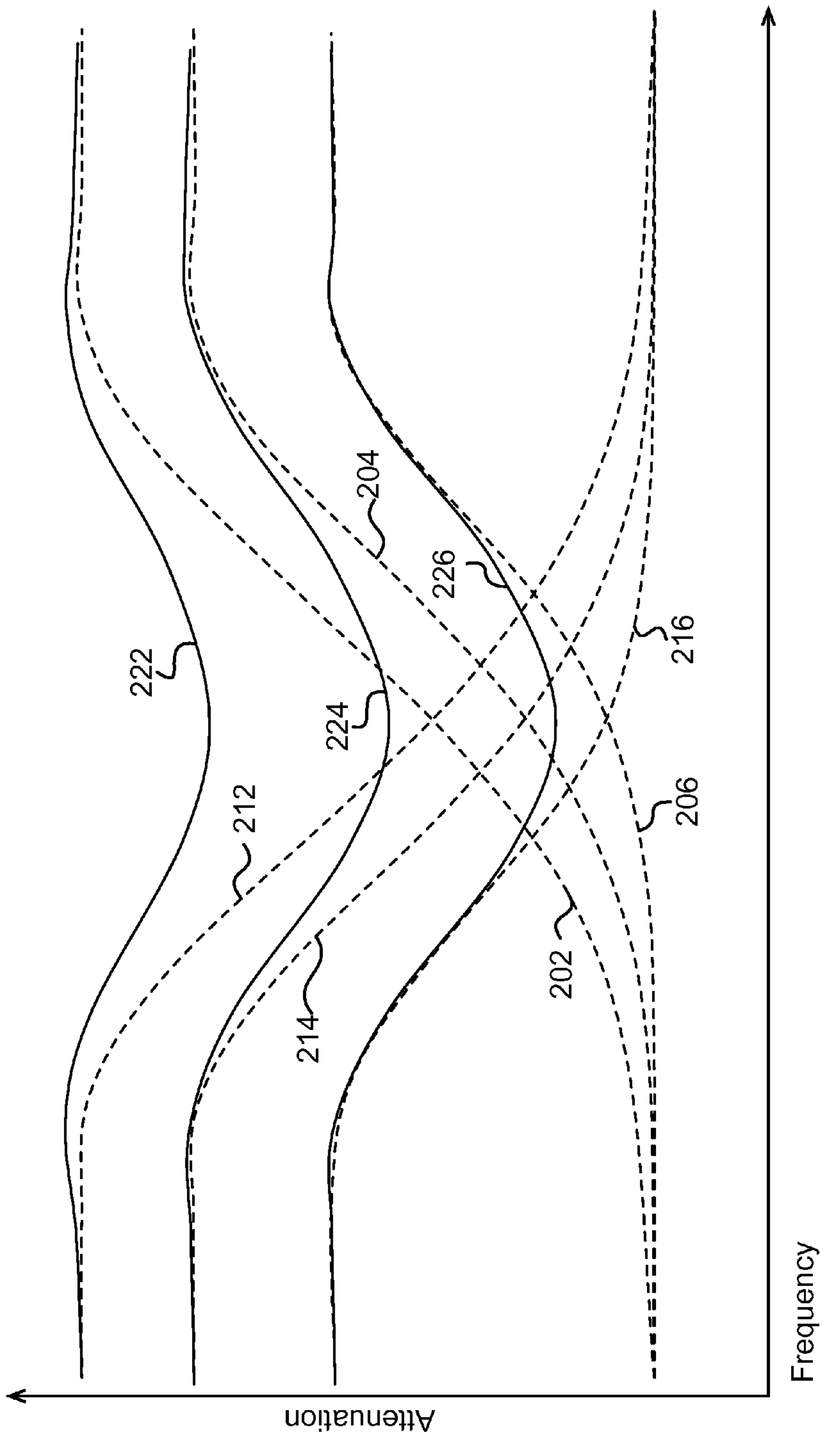
FIG. 2 shows a graph of attenuation curves.

FIG. 2 shows abstracted attenuation curves showing the relative noise reduction as a function of frequency for three configurations. Lines 202, 204, and 206 show the passive attenuation for three different amounts of clamping force. For the highest clamping force, line 202 shows the highest passive attenuation. For an intermediate clamping force, line 204 shows slightly less passive attenuation. For the lowest clamping force, line 206 shows the least passive attenuation. In all three situations, the passive attenuation is most significant at higher frequencies.

Lines 212, 214, and 216 show the active attenuation resulting from three different amounts of gain in the noise cancellation circuitry. For the highest clamping gain, line 212 shows the maximum active attenuation. For an intermediate gain, line 214 shows a slightly reduced active attenuation. For the lowest gain, line 216 shows the greatest reduction in active attenuation. Regardless of the gain, the active attenuation is most significant in lower frequencies.

The gain values may be paired with the corresponding clamping force amounts, such that for each clamping force value, the active attenuation is adjusted to correspond to the decrease in passive attenuation, such that the low-frequency attenuation and the high-frequency attenuation remain about the same. As a result, total attenuation lines 222, 224, and 226 correspond to matched sets 202 and 212, 204 and 214, and 206 and 216, respectively. Because the gain is adjusted to match the reduced clamping force, the overall shapes of all three total attenuation curves are roughly the same, simply the level is adjusted. This preserves the dynamic range and tonal balance for each of the clamping force values.

Figure 1B:
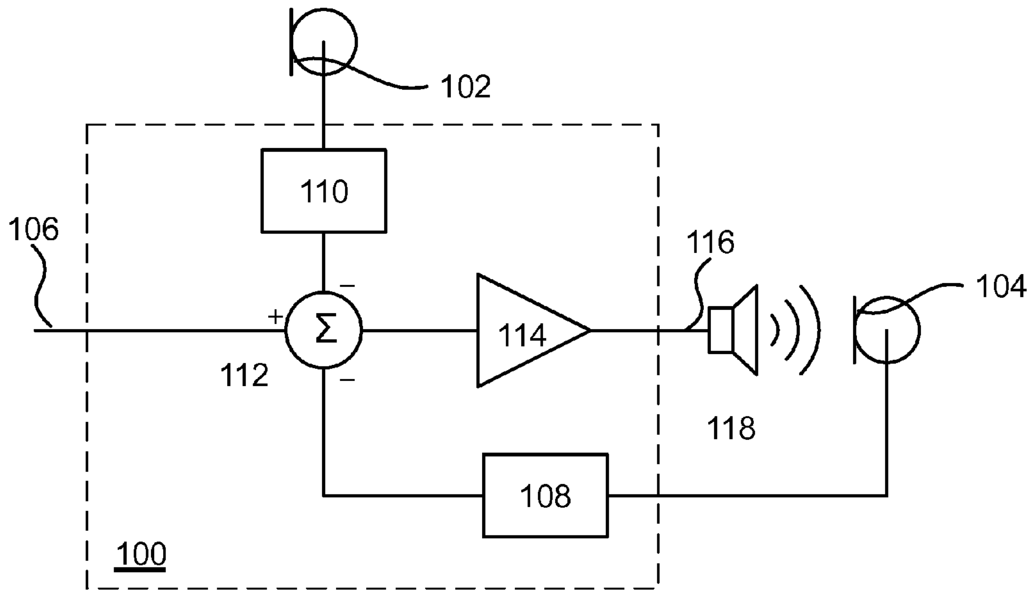
FIGS. 1B and 3 shows active noise reduction circuits.
Figure 3:
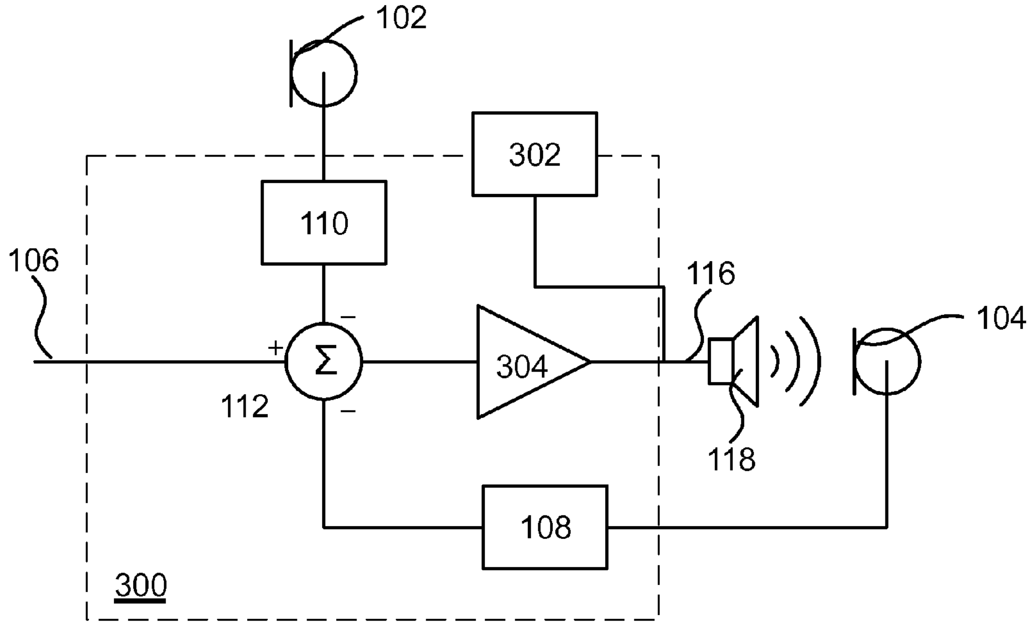

In one embodiment, as shown in FIG. 3, an ANR circuit 300 in the headset detects that the clamping force has been reduced through an input 302. This detection may be accomplished in several ways, discussed below. In response, the gain 304 of the ANR circuit 300 is automatically adjusted to compensate for the decreased clamping force when generating the anti-noise signal 116 to be output by the transducer 118. Note that this does not necessarily mean that the ANR level is increased to offset the loss of passive noise reduction, though that is one possibility. In other cases, the ANR level is decreased along with the passive noise reduction, so that the ANR system does not begin to clip. As with the generic circuit 100 of FIG. 1B, the ANR circuit 300 in FIG. 3 may be implemented in analog or digital circuitry, or some combination of both. In an analog example, the clamping force input 302 may simply control a voltage level to a control input of an amplifier stage applying the gain 304, as is shown. In a digital example, the clamping force may be an input to an integrated digital signal processor (DSP) that applies the gain 304 internally and outputs the anti-noise signal 166. In some examples, the gains applied to whichever of the signal paths—feedback, feedforward, and audio input(s)—are present are each adjusted individually.

For pilots, several implementations may have value. In one example, both passive and active noise reduction may be increased during takeoff and landing, and decreased when cruising. Decreasing the clamping force when cruising provides increased comfort, and has the additional benefit of improved situational awareness, as the pilot is better-able to hear ambient sounds that aren't connected to the plane's intercoms, such as other crewmembers or passengers. The ANR during cruising mode may simply be decreased in level to avoid clipping, maintain tonal balance, and improve awareness, or it may additionally have its equalization adjusted to compensate for changes in the frequency response of the passive noise reduction. In some examples, the ANR filters (108 and/or 110 in FIG. 3) may be tuned to not cancel the voice-band as aggressively or at all, while continuing to filter out the background noise of the aircraft.

In another example, some users of ANR headphones wish to maintain some level of noise reduction at times when the headsets must be powered off, such as for passengers of commercial aircraft during takeoff and landing, or when the battery has died. In this case, the headsets may provide a mode where the clamping force is increased beyond what is needed when the ANR system is powered, to provide some additional passive noise reduction. Comfort is sacrificed, but the mode is normally only needed for a few minutes of each flight. In some examples, a mechanism for physically adjusting the clamping force is connected to the power supply for the ANR circuit. This allows loosening the fit to turn on the ANR circuit. In other examples, the normal state of the headphones may be to apply the higher clamping force, with the force reduced whenever the ANR circuit is powered. Several mechanisms for powered control of the clamping force are discussed below.

The amount of passive attenuation may be adjusted in various ways. At its simplest, for headsets with an adjustable fit, the user may simply loosen the adjustment. In typical headsets, the length of the headband can be adjusted to fit the headsets to different-sized heads. For a single user, increasing the length leads to a looser fit. While such a fit may also result in the earcups being presented to the head at a less desirable angle, it can nonetheless serve the purpose of decreasing passive noise reduction and increasing comfort. For situations where an adjustment between tight and loose is expected to occur regularly, a headset may provide a quick toggle between two settings, such as with a lever or knob that increases or decreases headband tension or length between two set positions. Another possible adjustment is the compliance of a pivoting part of the headset, such as the yoke connecting the earcups to the headband in the example of FIG. 1A. This has the advantage of decreasing clamping force without changing the angle between the earcup and the head.

Adjustments to fit may be automated, with motors or other active mechanisms connected to the adjustable parts and controlled by the ANR circuitry. Other ways of actively controlling the fit may include magnetic or pneumatic components in the earcup, cushion, or headband structures that are controlled electronically to change the mechanical properties or interactions of the components. In addition to changing the clamping force, passive attenuation may also be controlled by opening or closing leaks in the earcup, which again may be manual or automated.

Several methods may be used to detect changes to the passive noise reduction, so that the ANR system may respond in the manners described above. Sensors may be used to detect the physical configuration of the headset, including mechanical position sensors, strain gauges, or pressure sensors. If some sort of switch is used to adjust between passive configurations, that switch may be instrumented to provide an electrical signal of its state or state changes. Conversely, if the fit can be controlled electronically, the system may already be aware of what the fit state is or able to detect changes. One pressure sensor already present in many cases is the system microphone of a feedback based ANR system, that is, feedback microphone 104 in FIG. 3. By detecting changes in the steady-state pressure inside the earcup, the feedback microphone may be used to detect changes in fit. If both feedback and feedforward systems are used, the amount of passive noise reduction can be measured by comparing the two microphone signals. Changes in fit may be inferred from changes in the passive noise reduction, or the ANR system may simply respond directly to the actual passive noise reduction, without specifically having modes for different fit states.

Other implementations are within the scope of the following claims and other claims to which the applicant may be entitled.

What is claimed is:

1. A headset comprising:

first and second earcups each having a front opening adapted to be adjacent to a respective ear of a user and comprising an electroacoustic transducer;

a headband coupled to each of the earcups; and an active noise reduction circuit coupled to the electroacoustic transducers;

wherein the headband is configurable between at least two on-head configurations that each press the earcups against the head of the user with different amounts of force without continued application of external force; and the active noise reduction circuit is configured to determine which of the at least two on-head configurations the headband is configured in based on signals received from a microphone, to provide a different amount of active noise reduction when the headband is configured in each of the different amounts of force, and to automatically transition between the different amounts of active noise reduction in response to a change in the configuration of the headband between the at least two configurations.

2. The headset of claim 1 further comprising a sensor disposed on the headband to detect the headband configuration.

3. The headset of claim 1 further comprising a sensor disposed inside the first earcup to detect the amount of force with which the earcup is pressed against the head of the user.

4. A headset comprising:

first and second earcups each having a front opening adapted to be adjacent to a respective ear of a user and comprising an electroacoustic transducer;

a headband coupled to each of the ear cups and configurable between at least two configurations that each press the earcups against the head of the user with different amounts of force; and an active noise reduction circuit coupled to the electroacoustic transducers;

wherein the active noise reduction circuit is configured to determine which of the at least two configurations the headband is configured in based on an output of the sensor, to provide a different amount of noise reduction when the headband is configured in each of the different amounts of force, to automatically transition between the different amounts of noise reduction in response to a change in the configuration of the headband between the at least two configurations, and to apply noise reduction having a different frequency response when the headband is configured in each of the different amounts of force.

5. The headset of claim 1 wherein the headband further comprises a user-actuated adjustment control to select between the different amounts of force.

6. The headset of claim 1 wherein the amount of force applied by the headband is controlled electronically.

7. The headset of claim 1 wherein for a first amount of force applied by the headband, the active noise reduction circuit provides no noise reduction.

8. The headset of claim 7 further comprising a power supply and control electronics, wherein the control electronics are configured to decouple the power supply from the active noise reduction circuit when the headband is applying the first amount of force, and to couple the power supply to the active noise reduction circuitry when the headband is applying a second amount of force.

9. The headset of claim 8 wherein the second amount of force is less than the first amount of force.

10. The headset of claim 8 wherein the control electronics comprise a switch activated by adjustment of the amount of force applied by the headband.

11. The headset of claim 1 wherein the active noise reduction circuit is further configured to apply noise reduction having a different frequency response when the headband is configured in each of the different amounts of force.

12. The headset of claim 11 wherein:

the active noise reduction circuit has at least two modes, the first mode providing a first amount of noise reduction when the headband is configured to provide a first amount of force, and the second mode providing a second amount of noise reduction when the headband is configured to provide a second amount of force, the second amount of noise reduction reducing more total noise than the first amount of noise reduction; and the second mode reduces low-frequency noise to a greater extent than the first mode, and reduces high-frequency noise to the same extent as the first mode.

13. The headset of claim 1 wherein the active noise reduction circuit is further configured to control the frequency response of the overall noise reduction of the headset such that the overall frequency response is generally independent of the amount of force applied by the headband.

14. The headset of claim 1 wherein the active noise reduction circuit is further configured to control the frequency response of the overall noise reduction of the headset such that the dynamic range of the overall noise reduction of the headset is generally independent of the amount of force applied by the headband.

15. The headset of claim 1 wherein the first and second earcups are each coupled to a respective first and second cushion, the earcups and first and second cushions sized such that the cushions couple the earcups to the head of the user around the user's ears.

16. The headset of claim 1 wherein the first and second earcups are each coupled to a respective first and second cushion, the earcups and first and second cushions sized such that the cushions couple the earcups to the pinnas of a user's ears.

17. A method of controlling an active noise-reducing headset having a headband having at least first and second on-head configurations that each press first and second earcups of the headset against the head of a user with different amounts of force without continued application of external force, the method comprising, in an active noise reduction circuit of the headset:

receiving signals from a microphone, determining whether the headband is configured in the first or the second configuration based on the signals received from the microphone, provide a first or a second amount of active noise reduction according to the determination of whether the headband is configured in the first or the second configuration, detecting a change in the configuration of the headband between the first and second configurations, and automatically transitioning between the first and second amounts of active noise reduction in response to the detected change in the configuration of the headband.

18. The method of claim 17 further comprising:

applying noise reduction having a different frequency response according to the determination of whether the headband is configured in the first or the second configuration.

19. The method of claim 17 further comprising:

controlling the frequency response of the overall noise reduction of the headset such that the overall frequency response is generally independent of the amount of force applied by the headband.

20. The method of claim 17 further comprising:

controlling the frequency response of the overall noise reduction of the headset such that the dynamic range of the overall noise reduction of the headset is generally independent of the amount of force applied by the headband.

21. A headset comprising:

first and second earcups each having a front opening adapted to be adjacent to a respective ear of a user and comprising an electroacoustic transducer;

a headband coupled to each of the ear cups and configurable between at least two configurations that each press the earcups against the head of the user with different amounts of force;

an active noise reduction circuit coupled to the electroacoustic transducers; and a sensor disposed on the headband to detect the headband configuration wherein the active noise reduction circuit is configured to determine which of the at least two configurations the headband is configured in based on an output of the sensor, to provide a different amount of noise reduction when the headband is configured in each of the different amounts of force, and to automatically transition between the different amounts of noise reduction in response to a change in the configuration of the headband between the at least two configurations.

22. The headset of claim 21 wherein the headband further comprises a user-actuated adjustment control to select between the different amounts of force.

23. The headset of claim 21 wherein for a first amount of force applied by the headband, the active noise reduction circuit provides no noise reduction.

24. The headset of claim 23 further comprising a power supply and control electronics, wherein the control electronics are configured to decouple the power supply from the active noise reduction circuit when the headband is applying the first amount of force, and to couple the power supply to the active noise reduction circuitry when the headband is applying a second amount of force.

25. The headset of claim 21 wherein the active noise reduction circuit is further configured to apply noise reduction having a different frequency response when the headband is configured in each of the different amounts of force.

26. The headset of claim 21 wherein:

the active noise reduction circuit has at least two modes, the first mode providing a first amount of noise reduction when the headband is configured to provide a first amount of force, and the second mode providing a second amount of noise reduction when the headband is configured to provide a second amount of force, the second amount of noise reduction reducing more total noise than the first amount of noise reduction; and the second mode reduces low-frequency noise to a greater extent than the first mode, and reduces high-frequency noise to the same extent as the first mode.

27. The headset of claim 21 wherein the active noise reduction circuit is further configured to control the frequency response of the overall noise reduction of the headset such that the overall frequency response is generally independent of the amount of force applied by the headband.

28. The headset of claim 21 wherein the active noise reduction circuit is further configured to control the frequency response of the overall noise reduction of the headset such that the dynamic range of the overall noise reduction of the headset is generally independent of the amount of force applied by the headband.

29. A headset comprising:

first and second earcups each having a front opening adapted to be adjacent to a respective ear of a user and comprising an electroacoustic transducer;

a headband coupled to each of the ear cups and configurable between at least two configurations that each press the earcups against the head of the user with different amounts of force;

an active noise reduction circuit coupled to the electroacoustic transducers; and a microphone disposed within the first ear cup;

wherein the active noise reduction circuit is configured to determine which of the at least two configurations the headband is configured in based on signals received from a microphone, to provide a different amount of noise reduction when the headband is configured in each of the different amounts of force, and to automatically transition between the different amounts of noise reduction in response to a change in the configuration of the headband between the at least two configurations.

30. The headset of claim 29 wherein the headband further comprises a user-actuated adjustment control to select between the different amounts of force.

31. The headset of claim 29 wherein for a first amount of force applied by the headband, the active noise reduction circuit provides no noise reduction.

32. The headset of claim 31 further comprising a power supply and control electronics, wherein the control electronics are configured to decouple the power supply from the active noise reduction circuit when the headband is applying the first amount of force, and to couple the power supply to the active noise reduction circuitry when the headband is applying a second amount of force.

33. The headset of claim 29 wherein the active noise reduction circuit is further configured to apply noise reduction having a different frequency response when the headband is configured in each of the different amounts of force.

34. The headset of claim 29 wherein:

the active noise reduction circuit has at least two modes, the first mode providing a first amount of noise reduction when the headband is configured to provide a first amount of force, and the second mode providing a second amount of noise reduction when the headband is configured to provide a second amount of force, the second amount of noise reduction reducing more total noise than the first amount of noise reduction; and the second mode reduces low-frequency noise to a greater extent than the first mode, and reduces high-frequency noise to the same extent as the first mode.

35. The headset of claim 29 wherein the active noise reduction circuit is further configured to control the frequency response of the overall noise reduction of the headset such that the overall frequency response is generally independent of the amount of force applied by the headband.

36. The headset of claim 29 wherein the active noise reduction circuit is further configured to control the frequency response of the overall noise reduction of the headset such that the dynamic range of the overall noise reduction of the headset is generally independent of the amount of force applied by the headband.

37. A headset comprising:

first and second earcups each having a front opening adapted to be adjacent to a respective ear of a user and comprising an electroacoustic transducer;

a headband coupled to each of the ear cups and configurable between at least two configurations that each press the earcups against the head of the user with different amounts of force, the amount of force being controlled electronically;

an active noise reduction circuit coupled to the electroacoustic transducers; and wherein the active noise reduction circuit is configured to determine which of the at least two configurations the headband is configured in based on the electronically controlled amount of force, to provide a different amount of noise reduction when the headband is configured in each of the different amounts of force, and to automatically transition between the different amounts of noise reduction in response to a change in the configuration of the headband between the at least two configurations.

38. The headset of claim 37 wherein the headband further comprises a user-actuated adjustment control to select between the different amounts of force.

39. The headset of claim 37 wherein for a first amount of force applied by the headband, the active noise reduction circuit provides no noise reduction.

40. The headset of claim 39 further comprising a power supply and control electronics, wherein the control electronics are configured to decouple the power supply from the active noise reduction circuit when the headband is applying the first amount of force, and to couple the power supply to the active noise reduction circuitry when the headband is applying a second amount of force.

41. The headset of claim 37 wherein the active noise reduction circuit is further configured to apply noise reduction having a different frequency response when the headband is configured in each of the different amounts of force.

42. The headset of claim 37 wherein:

the active noise reduction circuit has at least two modes, the first mode providing a first amount of noise reduction when the headband is configured to provide a first amount of force, and the second mode providing a second amount of noise reduction when the headband is configured to provide a second amount of force, the second amount of noise reduction reducing more total noise than the first amount of noise reduction; and the second mode reduces low-frequency noise to a greater extent than the first mode, and reduces high-frequency noise to the same extent as the first mode.

43. The headset of claim 37 wherein the active noise reduction circuit is further configured to control the frequency response of the overall noise reduction of the headset such that the overall frequency response is generally independent of the amount of force applied by the headband.

44. The headset of claim 37 wherein the active noise reduction circuit is further configured to control the frequency response of the overall noise reduction of the headset such that the dynamic range of the overall noise reduction of the headset is generally independent of the amount of force applied by the headband.

45. The headset of claim 4 wherein the active noise reduction circuit is configured to determine the headband configuration based on signals received from a microphone.

46. The headset of claim 4 wherein the headband further comprises a user-actuated adjustment control to select between the different amounts of force.

47. The headset of claim 4 further comprising a sensor disposed on the headband to detect the headband configuration.

48. The headset of claim 4 wherein the active noise reduction circuit is configured to determine the headband configuration based on signals received from a microphone.

49. The headset of claim 4 wherein the amount of force applied by the headband is controlled electronically.

50. The headset of claim 4 wherein the active noise reduction circuit is further configured to control the frequency response of the overall noise reduction of the headset such that the overall frequency response is generally independent of the amount of force applied by the headband.

51. The headset of claim 4 wherein the active noise reduction circuit is further configured to control the frequency response of the overall noise reduction of the headset such that the dynamic range of the overall noise reduction of the headset is generally independent of the amount of force applied by the headband.

52. A headset comprising:

first and second earcups each having a front opening adapted to be adjacent to a respective ear of a user and comprising an electroacoustic transducer;

a headband coupled to each of the ear cups and configurable between at least two configurations that each press the earcups against the head of the user with different amounts of force; and an active noise reduction circuit coupled to the electroacoustic transducers;

wherein the active noise reduction circuit is configured to determine which of the at least two configurations the headband is configured in, to provide a different amount of noise reduction when the headband is configured in each of the different amounts of force, to automatically transition between the different amounts of noise reduction in response to a change in the configuration of the headband between the at least two configurations, and to control the frequency response of the overall noise reduction of the headset such that the overall frequency response is generally independent of the amount of force applied by the headband.

53. The headset of claim 52 wherein the active noise reduction circuit is further configured to control the frequency response of the overall noise reduction of the headset such that the dynamic range of the overall noise reduction of the headset is generally independent of the amount of force applied by the headband.

54. The headset of claim 52 wherein the headband further comprises a user-actuated adjustment control to select between the different amounts of force.

55. The headset of claim 52 further comprising a sensor disposed on the headband to detect the headband configuration.

56. The headset of claim 52 wherein the active noise reduction circuit is configured to determine the headband configuration based on signals received from a microphone.

57. The headset of claim 52 wherein the amount of force applied by the headband is controlled electronically.

58. A headset comprising:

first and second earcups each having a front opening adapted to be adjacent to a respective ear of a user and comprising an electroacoustic transducer;

a headband coupled to each of the ear cups and configurable between at least two configurations that each press the earcups against the head of the user with different amounts of force; and an active noise reduction circuit coupled to the electroacoustic transducers;

wherein the active noise reduction circuit is configured to determine which of the at least two configurations the headband is configured in, to provide a different amount of noise reduction when the headband is configured in each of the different amounts of force, to automatically transition between the different amounts of noise reduction in response to a change in the configuration of the headband between the at least two configurations, and to control the frequency response of the overall noise reduction of the headset such that the dynamic range of the overall noise reduction of the headset is generally independent of the amount of force applied by the headband.

59. The headset of claim 58 wherein the headband further comprises a user-actuated adjustment control to select between the different amounts of force.

60. The headset of claim 58 further comprising a sensor disposed on the headband to detect the headband configuration.

61. The headset of claim 58 wherein the active noise reduction circuit is configured to determine the headband configuration based on signals received from a microphone.

62. The headset of claim 58 wherein the amount of force applied by the headband is controlled electronically.

* * * * *